(12) United States Patent
Haga et al.

(10) Patent No.: US 6,620,945 B2
(45) Date of Patent: Sep. 16, 2003

(54) PROCESS FOR PRODUCING STEREOISOMER OF PYRROLIDINE DERIVATIVE

(75) Inventors: Toyokazu Haga, Ibaraki (JP); Akio Kayano, Ibaraki (JP); Manabu Sasyou, Tsukuba (JP); Shigeto Negi, Tsukuba (JP); Hiroyuki Naka, Tsukuba (JP); Hirofumi Noda, Kitaibaraki (JP); Ken-ichi Sakai, Kitaibaraki (JP)

(73) Assignees: Eisai Co., Ltd., Tokyo (JP); Yamakawa Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/142,339

(22) Filed: May 8, 2002

(65) Prior Publication Data

US 2003/0004208 A1 Jan. 2, 2003

(30) Foreign Application Priority Data

May 9, 2001 (JP) ........................ 2001-138370

(51) Int. Cl.⁷ ............................ C07D 201/00
(52) U.S. Cl. ...................................... 548/541
(58) Field of Search .......................... 548/541

(56) References Cited

FOREIGN PATENT DOCUMENTS

JP          WO 01/23383          4/2001       ......... C07D/453/02

OTHER PUBLICATIONS

Okada, T., et al., *Chemical and Pharmaceutical Bulletin*, vol. 41. No. 1, 1993 pp. 132–138.
Eliel, E.L., et al., *Stereochemistry of Organic Compounds*, 1994, John Wiley & Sons, Inc., Chapter 7–3, pp. 322–381.
De Sousa, S.E., et al., *Tetrahedron : Asymmetry*, vol. 8, No. 15, 1997, pp. 2613–2618.
Lin, J., et al., *Tetrahedron Letters*, vol. 41, 2000, pp. 2949–2951.

*Primary Examiner*—Joseph K. McKane
*Assistant Examiner*—Rei Tsang Shiao
(74) *Attorney, Agent, or Firm*—Morgan & Finnegan, L.L.P.

(57) ABSTRACT

The present invention provides a process for producing optically active 3-hydroxy-4-methoxypyrrolidine, which is an intermediate for synthesizing a quinuclidine derivative useful as a squalene synthetase inhibitor, a salt thereof, or a hydrate thereof by subjecting a pyrrolidine derivative represented by the following formula (1-4):

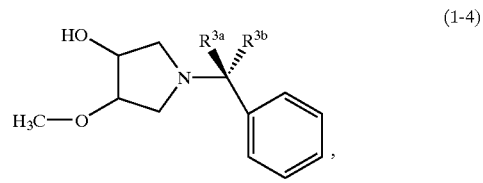

wherein $R^{3a}$ and $R^{3b}$ are different and each of $R^{3a}$ and $R^{3b}$ represents a hydrogen atom or a methyl group, to optical division purification by using an optically active dibenzoyl-tartaric acid derivative or the like.

20 Claims, No Drawings

PROCESS FOR PRODUCING STEREOISOMER OF PYRROLIDINE DERIVATIVE

FIELD OF THE INVENTION

The present invention relates to a process for producing an optically active 3-hydroxy-4-methoxypyrrolidine, which is a synthesis intermediate of a quinuclidine derivative useful, as a squalene synthetase inhibitor, for prevention and treatment of hyperlipemia such as arteriosclerotic disease, ischemic heart disease and the like.

BACKGROUND OF THE INVENTION

At present, an HMG-CoA reductase inhibitor is widely used as a cholesterol-decreasing agent. Since this inhibitor produces an effect on metabolic materials other than cholesterol, a side effect thereof is becoming a problem. A squalene synthetase functions in the lower course than an HMG-CoA reductase and an isoprene synthesis system in the biosynthesis system of cholesterol. Therefore, it is expected that the squalene synthetase overcomes the side effect problem of the HMG-CoA reductase inhibitor. However, no squalene synthetase inhibitor which produces only a small side effect and exhibits sufficient efficacy as hyperlipemia therapeutic agent has been created before.

After eager researches, the present inventors found that a quinuclidine derivative comprising 3-hydroxy-4-methoxypyrrolidine or the like has a superior squalene synthetase inhibiting effect and is useful as a hyperlipemia therapeutic agent. The inventors then filed a Patent Application about the quinuclidine derivative (WO 01/23383).

In a process for producing a quinuclidine derivative comprising 3-hydroxy-4-methoxypyrrolidine or the like, described in this Patent Application (WO 01/23383), 3-hydroxy-4-methoxypyrrolidine, which is concerned with the present invention, is not used as an intermediate. Therefore, this process is unsatisfactory as an industrial process for producing the quinuclidine derivative in light of a large number of the steps included in the process and the yield thereof as a whole. 3-Hydroxy-4-methoxypyrrolidine is new as a racemic body or an optically active substance, and has not been known so far.

SUMMARY OF THE INVENTION

An object of the present invention is to provide a useful process for producing optically active 3-hydroxy-4-methoxypyrrolidine, which is an intermediate for producing the above-mentioned quinuclidine derivative.

In the present invention, 3-hydroxy-4-methoxypyrrolidine is used. Therefore, the number of steps in the method of the present invention can be smaller than that of the above-mentioned process (WO 01/23383). Accordingly, the present invention can be used to produce the quinuclidine derivative effectively and industrially.

The inventors have found out a useful process for producing optically active 3-hydroxy-4-methoxypyrrolidine, that is, the following inventions <1> to <11>:

<1> A process for producing optically active 3-hydroxy-4-methocypyrrolidine represented by the following formula (1-7):

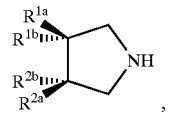

(1-7)

wherein $R^{1a}$ and $R^{1b}$ are different from each other, and each of $R^{1a}$ and $R^{1b}$ represents a hydrogen atom or a hydroxyl group, and $R^{2a}$ and $R^{2b}$ are different from each other, and each of $R^{2a}$ and $R^{2b}$ represents a hydrogen atom or a methoxy group], a salt thereof or a hydrate thereof, comprising the steps of:

subjecting a pyrrolidine derivative represented by the following formula (1-4):

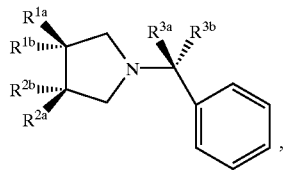

(1-4)

wherein $R^{1a}$, $R^{1b}$, $R^{2a}$ and $R^{2b}$ have the same definition as mentioned above, and $R^{3a}$ and $R^{3b}$ are different 1 mm each other, and each of $R^{3a}$ and $R^{3b}$ represents a hydrogen atom or a methyl group, to optical division purification by using an optically active dibenzoyltartaric acid derivative represented by the following formula (1-5):

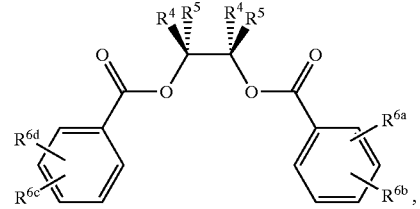

(1-5)

wherein $R^{6a}$, $R^{6b}$, $R^{6c}$ and $R^{6d}$ each independently represents a hydrogen atom, a halogen atom, a C1–6 alkoxy group or a C1–6 alkyl group, and $R^4$ and $R^5$ are different tram each other, and each of $R^4$ end $R^5$ represents a hydrogen atom or a carboxyl group, to yield a compound (1-6) represented by the following formula (1-6):

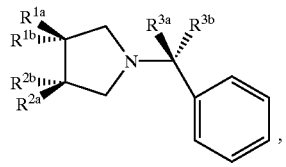

(1-6)

wherein $R^{1a}$, $R^{1b}$, $R^{2a}$, $R^{2b}$, $R^{3a}$ and $R^{3b}$ have the same definition as mentioned above; and removing the 1-phenylethyl group of the compound (1-6), to yield the 3-hydroxy-4-methoxypyrrolidine, the salt thereof or the hydrate thereof;

<2> A process for producing optically active 3-hydroxy-4-methoxypyrrolidine represented by the following formula (1-7):

(1-7)

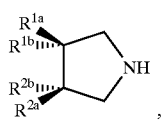

wherein $R^{1a}$ and $R^{1b}$ are different from each other, and each of $R^{1a}$ and $R^{1b}$ represents a hydrogen atom or a hydroxyl group and $R^{2a}$ and $R^{2b}$ are different from each other, and each of $R^{2a}$ and $R^{2b}$ represents a hydrogen atom or a methoxy group, a salt thereof or a hydrate thereof, comprising the steps of:

reacting an oxysilafle derivative represented by the following formula (1-1)

(1-1)

wherein $L^1$ represents a halogen atom, a methanesulfonyloxy group or a p-toluenesulfonyloxy group, with an amine derivative represented by the following formula (1-2)

(1-2)

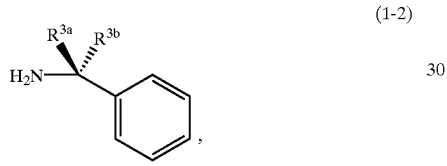

wherein $R^{3a}$ and $R^{3b}$ are different from each other, and each of $R^{3a}$ and $R^{3b}$ represents a hydrogen atom or a methyl group, to yield a pyrrolidine derivative (1-3) represented by the following formula (1-3):

(1-3)

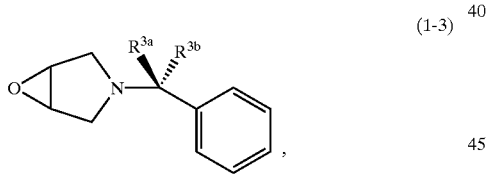

wherein $R^{3a}$ and $R^{3b}$ have the same definition as mentioned above;

reacting the derivative (1-3) with a methoxylating agent, to yield a pyrrolidine derivative (1-4):

(1-4)

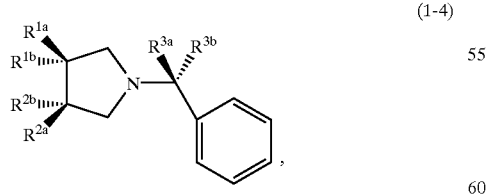

wherein $R^{1a}$, $R^{1b}$, $R^{2a}$, $R^{2b}$, $R^{3a}$ and $R^{3b}$ have the same definition as mentioned above;

subjecting the derivative (1-4) to optical division purification by using an optically active dibenzoyltartaric acid derivative represented by the following formula (1-5):

(1-5)

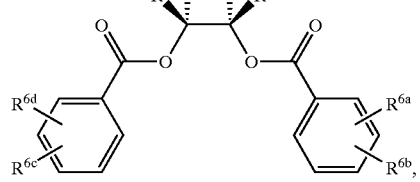

wherein $R^{6a}$, $R^{6b}$, $R^{6c}$ and $R^{6d}$ each independently represents a hydrogen atom, a halogen atom, a C1–6 alkoxy group or a C1–6 alkyl group, and $R^4$ and $R^5$ are different from each other, and each of $R^4$ and $R^5$ represents a hydrogen atom or a carboxyl group, to yield a compound (1-6) represented by the following formula (1-6):

(1-6)

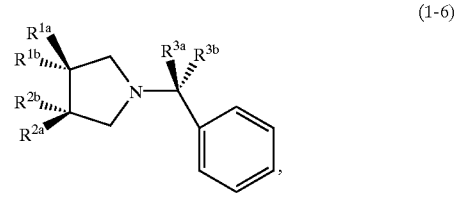

wherein $R^{1a}$, $R^{1b}$, $R^{2a}$, $R^{2b}$, $R^{3a}$ and $R^{3b}$ have the same definition as mentioned above; and removing the 1-phenylethyl group of the compound (1-8), to yield the 3-hydroxy-4-methoxypyrrolidine, the salt thereof or the hydrate thereof;

<3> The method according to the above-mentioned item <1> or <2>, wherein each of $R^{1a}$ and $R^{2b}$ represents a hydrogen atom;

<4> The method according to the above-mentioned item <1> or <2>, wherein each of $R^{1b}$ and $R^{2a}$ represents a hydrogen atom;

<5> The method according to any one of the above-mentioned items <1> to <4>, wherein $R^{3a}$ represents a methyl group;

<6> The method according to any one of the above-mentioned items <1> to <4>, wherein $R^{3b}$ represents a methyl group;

<7> The method according to any one of the above-mentioned items <1> to <6>, wherein said compound (1-4) represents a mixture of compounds represented by the following formulae (1-4a) and (1-4b) (wherein $R^{3a}$ and $R^{3b}$ are different from each other, and each of $R^{3a}$ and $R^{3b}$ represents hydrogen atom or a methyl group), in which the mixture having a given mixture ratio of compound (1-4a) to (1-4b):

(1-4a)

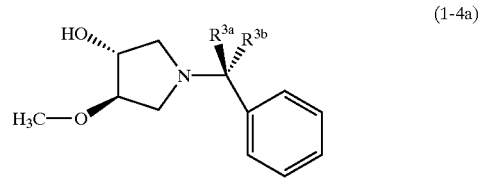

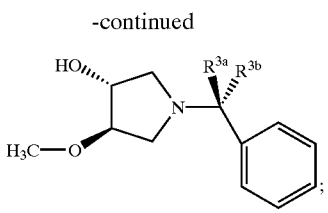

(1-4b)

<8> The method according to the above-mentioned item <7>, wherein said compound (1-4) is said mixture of said compounds (1-4a) and (1-4b) having a ratio of 1:1 of said compounds (1-4a) to (1-4b);

<9> The method according to any one of the above-mentioned items <1> to <8>, wherein $R^4$ represents a hydrogen atom;

<10> The method according to any one of the above-mentioned items <1> to <8>, wherein $R^5$ represents a hydrogen atom; and <11> The method according to any one of the above-mentioned items <1> to <10>, wherein each of $R^{6a}$, $R^{6b}$, $R^{6c}$ and $R^{6d}$ represents a hydrogen atom.

DETAILED DESCRIPTION OF THE REFERRED EMBODIMENT

The present invention will be described in detail hereinafter.

First, meanings of terms, symbols and the like described hereinafter will be defined.

In the present specification and claims, a structural formula of a compound may conveniently represent a given isomer. Compounds of the present invention may be isomers thereof such as all geometrical isomers generated from the structure of the compounds, optical isomers based on an asymmetric carbon thereof, stereoisomers and enantiomers, and mixtures of some of the isomers. Accordingly, the compounds of the present invention are not limited to those defined by the structural formula thereof, and may be any one of the isomers, or a mixture of some of the isomers. Some compounds of the present invention may have an asymmetric carbon in the molecule thereof, and thus may be optically active substances thereof or racemic bodies thereof. The compounds of the present invention may have crystal polymorphisms, but are not limited to the crystal form thereof. The compounds of the present invention may be in a single crystal form or in a mixed crystal form. Furthermore, the compounds of the present invention may be in a dehydrate form or in a hydrate form.

In the present specification and claims, the term "C1–6 alkyl group" means a linear or branched alkyl group having 1 to 6 carbon atoms. Specific examples thereof include methyl, ethyl, n-propyl, i-propyl, n-butyl, i-butyl, t-butyl, n-pentyl, i-pentyl, neopentyl, n-hexyl, 1-methylpropyl, 1,2-dimethylpropyl, 2-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl, and 3-methylpentyl groups.

In the present specification and claims, the term "halogen atom" means a fluorine, chlorine, bromine or iodine atom.

In the present specification and claims, the term "C1–6 alkoxy group" means an oxy group to which the above-defined "C1–6 alkyl group" is bonded. Specific examples thereof include methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy, i-hexyloxy, 1-methylpentyloxy, 2-methylpentyloxy, 3-methylpentyloxy, 1,1-dimethylbutoxy, 1,2-dimethylbutoxy, 2,2-dimethylbutoxy, 1,3-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy groups.

The methoxylating agent means a sodium methoxide, potassium methoxide, magnesium methoxide or the like, or a solution thereof. The solvent of the solution may be an organic solvent such as methanol.

The optically active dibenzoyltartaric acid derivative (1-5) is an optically active compound (1-5) represented by the following formula:

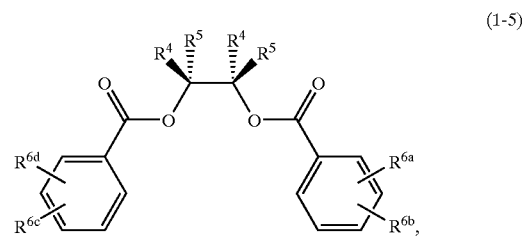

(1-5)

wherein $R^{6a}$, $R^{6b}$, $R^{6c}$ and $R^{6d}$ each independently represents a hydrogen atom, a halogen atom, a C1–6 alkoxy group or a C1–6 alkyl group, $R^4$ and $R^5$ are different from each other, and each of $R^4$ and $R^5$ represents a hydrogen atom or a carboxyl group; a salt thereof, or salts thereof. The present compound (1-5) is preferably a hydrate of D-dibenzoyltartaric acid or L-dibenzoyltartaric acid, and is more preferably a monohydrate of D-dibenzoyltartaric acid.

Specific examples of the compound (1-6) may include compounds represented by the following formula:

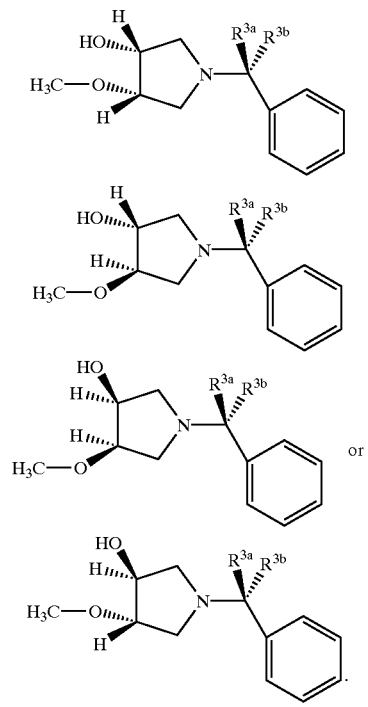

Preferred specific examples may be compounds represented by the following formula:

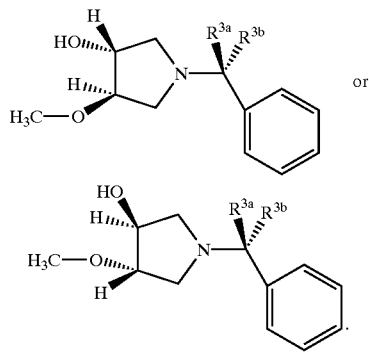

A more preferred specific example may be a compound represented by the following formula:

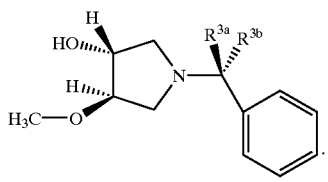

Specific examples of the compound (1-7) may include compounds represented by the following formula:

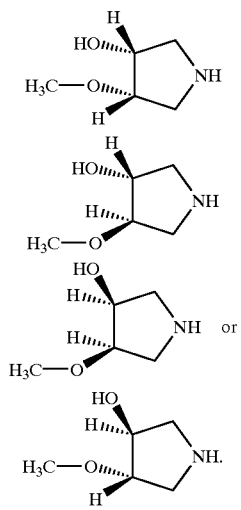

Preferred specific examples may be compounds represented by the following formula:

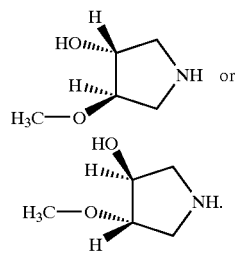

A more preferred specific example may be a compound represented by the following formula:

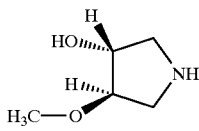

The salt referred to in the present invention may include, but is not limited to, inorganic salts such as hydrofluorides, hydrochlorides, sulfates, nitrates, perchlorates, phosphates, carbonates, bicarbonates, hydrobromates, hydroiodides and the like; salts of organic carboxylic acids such as acetates, maleates, fumarates, oxalates, lactates, tartrates, trifluoroacetates and the like; organic sulfonates such as methanesulfonates, trifluoromethanesulfonates, ethanesulfonates, hydroxymethanesulfonates, hydroxyethanesulfoantes, benzenesulfonates, toluenesulfonates, taurine salts and the like; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts, phenetylbenzylamine salts and the like; alkali metal salts such as sodium salts, potassium salts and the like; alkali earth metal salts such as magnesium salts, calcium salts and the like; and amino acid salts such as arginine salts, lysine salts, serine salts, glycine salts, aspartate salts, glutamate salts and the like. Preferably, pharmaceutically acceptable salts are used.

The compound of the present invention represented by the following general formula can be synthesized by a conventionally known organic chemistry reaction and the like:

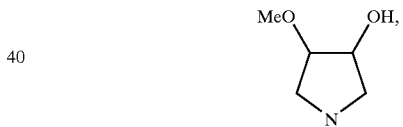

For example, the compound can be synthesized by the following process: Synthesis method:

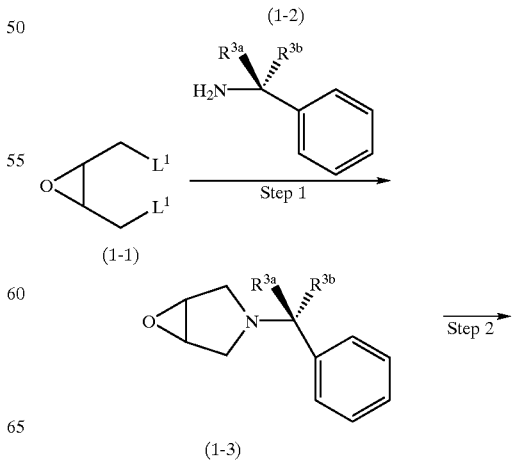

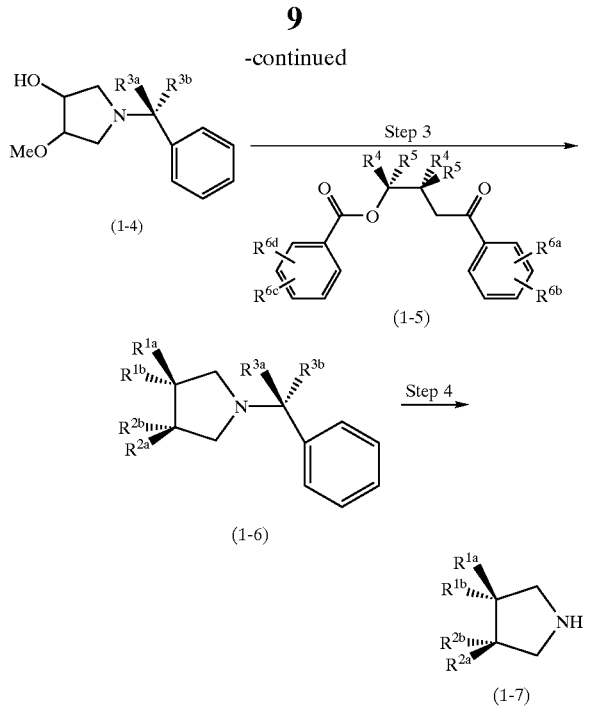

wherein $L^1$, $R^{1a}$, $R^{1b}$, $R^{2a}$, $R^{2b}$, $R^{3a}$, $R^{3b}$, $R^4$, $R^5$, $R^{6a}$, $R^{6b}$, $R^{6c}$ and $R^{6d}$ have the same definition as mentioned above.

Step 1

A benzylamine derivative (1-2) can be reacted with a compound (1-1), to obtain a compound (1-3). In the reaction, a base may be added to the reaction system. Specific examples of the base which can be used include nitrogen-containing bases such as triethylamine, N-methylmorpholine, pyridine and the like; and inorganic bases such as sodium carbonate, potassium carbonate, sodium hydrogen carbonate and the like. Examples of a solvent for the reaction include acetone, esters such as ethyl acetate, ethers such as tetrahydrofuran and t-butyl methyl ether, lower nitriles such as acetonitrile, and aprotic solvents such as dimethylformamide, dimethyl sulfoxide and toluene. Reaction temperature may be from about 0 to 80° C., preferably from about 20 to 50° C. Reaction time may be 10 hours or more, usually 48 hours.

Step 2

Step 2 of the conversion of the compound (1-3) to a compound (1-4) is a step of subjecting the epoxide to ring-opening reaction. The compound (1-3) can be reacted with a methoxylating agent, to obtain the compound (1-4). Examples of the methoxylating agent that can be used may include alkali metal methoxides such as sodium methoxide, lithium methoxide and the like. A solvent for the reaction may be usually methanol. Tetrahydrofuran, dimethyl sulfoxide, toluene or the like may be added thereto. Reaction temperature may be usually 40° C. or more. Reaction time may be several hours.

Step 3

Step 3 is a step of yielding a compound (1-6) from the compound (1-4) by optical division purification.
Procedure 3-1
Procedure 3-1 is a procedure of forming a salt of a tartaric acid derivative and recrystallizing the salt.

The compound (1-4) is mixed with 0.5 to 2 equivalents of a compound (1-5), to form a salt (1-5b) of the compound (1-4) and the compound (1-5), followed by crystallizing the salt. The salt (1-5b) is subjected to purification based on plural recrystallization steps until the optical purity thereof comes up to a target value. Examples of a solvent for the recrystallization may include water; lower alkyl alcohols such as methanol, ethanol, propanol, isopropanol and the like; ketones such as acetone, methyl ethyl ketone and the like; acetate esters such as methyl acetate, ethyl acetate and the like; ethers such as tetrahydrofuran, t-butyl methyl ether and the like; aromatic compounds such as toluene and the like; and mixture thereof. Reaction temperature may be from −20 to 100° C. The time for the crystallization may be from 1 hour to 2 days, preferably from 4 hours to 24 hours.

Procedure 3-2

Procedure 3-2 is a procedure of freeing the salt (1-5b) of the tartaric acid derivative formed and purified by the procedure 3-1. To the salt (1-5b) is added an aqueous solution of an alkali metal salt such as a hydroxide, carbonate or the like, or ammonium water in an equivalent amount or more, so as to free the salt and obtain a compound (1-6). Then, the compound (1-6) is extracted with an organic solvent immiscible with water, for example, an acetate ester such as ethyl acetate or isopropyl acetate, or an ether such as t-butyl methyl ether, or an aromatic compound such as toluene. Reaction temperature may be typically from 10 to 30° C. Reaction time is within the range of several hours.

Step 4

Step 4 is a reducing step. The compound (1-6) is reduced in the presence of a palladium catalyst in the atmosphere of hydrogen, to yield a compound (1-7). Specific examples of the palladium catalyst may include Pd—C, Pd(OH)$_2$ and the like. A solvent that can be used for the reaction may be a solvent that does not react with hydrogen. Examples of the solvent may include alcohols such as methanol, ethanol, propanol and the like; esters such as ethyl acetate and the like; ethers such as tetrahydrofuran, t-butyl ether and the like. Reaction temperature may be from 0 to 100° C., and reaction time may be several hours.

After the end of the above-mentioned reaction, if desired, the resultant compound can be purified by a usual method, for example, column chromatography separation using silica gel, absorbing resin or the like, or recrystallization from a suitable solvent.

EXAMPLES

The present invention will be demonstrated by way of the following examples, but is in no way limited by these examples. "Me" described hereinafer represents a methyl group, and "Ms" described hereinafer represents a methylsufonyl group, hereinafter.

Example 1

(1'R)-1-(1'-phenylethyl)-3,4-epoxypyrrolidine (in a tetrahydrofuran solvent)

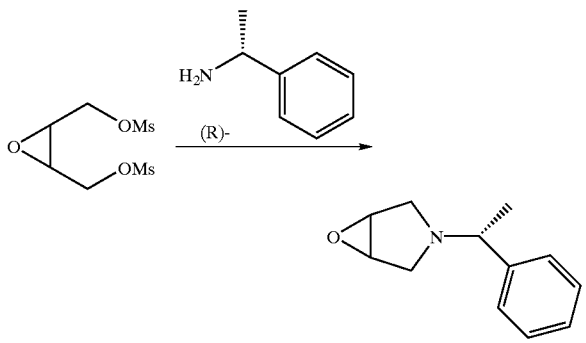

(R)-phenylethylamine (4.19 g, 34.6 mmol) was added to a solution of 1,4-dimethanesulfonyloxy-3,4-epoxybutane (see Carbohydrate Research, 56 (1977) pp. 43–52, Geza Schneider, Tibor Horvath, and Pal Sohar) (3.0 g, 11.5 mmol) in tetrahydrofuran (8.0 mL), and then the solution was stirred at room temperature for 3 days. The disappearance of the raw materials was determined by TLC (hexane/ethyl acetate=1/2). Thereafter, 2 mol/L of an aqueous sodium hydroxide solution (15 mL) was added to the reaction solution, and then the resultant solution was subjected to extraction with t-butyl methyl ether (12 mL) two times. The combined organic layers were washed with saturated salt water (6 mL), and were dried over anhydrous magnesium sulfate. The filtrate was concentrated to yield 4.49 g of a crude product. This was purified by silica gel chromatography (t-butyl methyl ether), to give 1.98 g of the captioned compound as a colorless oily material (yield: 91%).

$^1$H NMR (400 MHz, CDCl$_3$) δ:1.36 (3H, d, J=6.8 Hz), 2.27 (1H, dd, J=1.5, 11.2 Hz), 2.46 (1H, dd, J=1.5, 11.2 Hz), 3.02 (1H, d, J=11.7 Hz), 3.40 (1H, q, J=6.8 Hz), 3.43 (1H, d, J=10.2 Hz), 3.55 (1H, dd, J=1.0, 3.4 Hz), 3.64 (1H, dd, J=1.0, 3.4 Hz), 7.35–7.20 (5H, m).

Example 2

(1'R)-1-(1'-phenylethyl)-3,4-epoxypyrrolidine (in a acetonitrile solvent)

A solution of (R)-phenylethylamine (4.13 kg, 34.1 mol) in acetonitrile (3 L) was dropwise added to a solution of 1,4-dimethanesulfonyloxy-3,4-epoxybutane (see Carbohydrate Research, 56 (1977) pp. 43–52, Geza Schneider, Tibor Horvath, and Pal Sohar) (5.91 kg, 22.7 mmol) in acetonitrile (11.8 L) at 10° C. under stirring over 17 minutes, and then the solution was washed with 2.2 L of acetonitrile. Triethylamine (4.60 kg, 45.4 mol) was dropwise added to this solution over 13 minutes, and then this solution was washed with 0.8 L of acetonitrile. This mixed solution was stirred at 22 to 33° C. for 3 days. The advance of the reaction was determined by TLC (hexane/ethyl acetate=1/2). Thereafter, to the reaction solution were added t-butyl methyl ether (30 L) and an aqueous 1 mol/L sodium hydroxide solution (44.3 L) to perform extraction. The aqueous layer was subjected to re-extraction with t-butyl methyl ether (30 L). Thereafter, the organic layers were combined, and the resultant solution was washed with salt water (12 L). The solution was dried over anhydrous magnesium sulfate, and concentrated under reduced pressure to yield 19.6 kg of a solution containing 3.53 kg (yield: 82% on the basis on HPLC quantitative analysis) of the captioned compound as a crude product and excessive (R)-phenylethylamine (1.52 kg on the basis on HPLC quantitative analysis).

To this solution was added ethyl acetate (30 L) and then thereto was added triethylamine (1.50 kg, 14.8 mol) at 9° C. Under stirring, thereto was dropwise added a solution of benzoyl chloride (1.92 kg, 13.6 mol) in ethyl acetate (5.17 L) over 27 minutes while the temperature of the reaction solution was kept at 20° C. or less. The solution was then washed with ethyl acetate (0.8 L). The disappearance of (R)-phenylethylamine was determined by TLC (hexane/ethyl acetate=1/2). Thereafter, thereto was dropwise added 2 mol/L hydrochloric acid aqueous solution (11.8 L) over 20 minutes while the inside temperature was kept at 15° C. or less (pH of the aqueous layer: 1). At the same temperature, the organic layer was separated, and the aqueous layer was washed with ethyl acetate (22 L). Thereto was added t-butyl methyl ether (30 L) and then thereto was added an aqueous sodium hydroxide solution (10 L) so as to adjust the pH of the aqueous layer to 13. In this way, the solution was separated into two layers. The organic layer was washed with 30% salt water (12 L), dried over 2.96 kg of anhydrous magnesium sulfate, and concentrated under reduced pressure. The residue was subjected to substitution with 8 L of methanol and concentrated to yield a methanol solution containing 3.50 kg of the captioned compound (yield: 81%). NMR data were the same as in Example 1.

Example 3

(1'S)-1-(1'-phenylethyl-3,4-epoxypyrrolidine

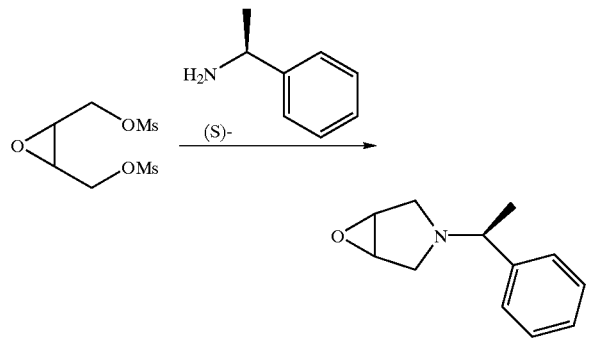

(S)-phenylethylamine (1.40 g, 11.5 mmol) was added to a solution of 1,4-dimethanesulfonyloxy-3,4-epoxybutane (see Carbohydrate Research, 56 (1977) pp. 43–52, Geza Schneider, Tibor Horvath, and Pal Sohar) (3.0 g, 11.5 mmol) in tetrahydrofuran (6.0 mL) under cooling with ice. Subsequently, thereto was added triethylamine (3.2 mL, 23.0 mmol). Thereafter, the solution was stirred at room temperature for 1 day.

Furthermore, (S)-phenylethylamine (1.40 g) was added to the solution, and at room temperature the solution was stirred for 3 days. The disappearance of the raw materials was determined by TLC (hexane/ethyl acetate=1/2). Thereafter, an aqueous 2 mol/L sodium hydroxide solution (15 mL) was added to the reaction solution, and then the resultant solution was subjected to extraction with t-butyl methyl ether (12 mL) two times. The combined organic layers were dried over anhydrous magnesium sulfate and concentrated to yield 3.42 g of a crude product. This was purified by silica gel chromatography (hexane:ethyl acetate=

1:1), to give 1.90 g of the captioned compound as a colorless oily material (yield: 87%).

Example 4

(1'R)-1-(1'-phenylethyl)-3-hydroxy-4-methoxy-pyrrolidine

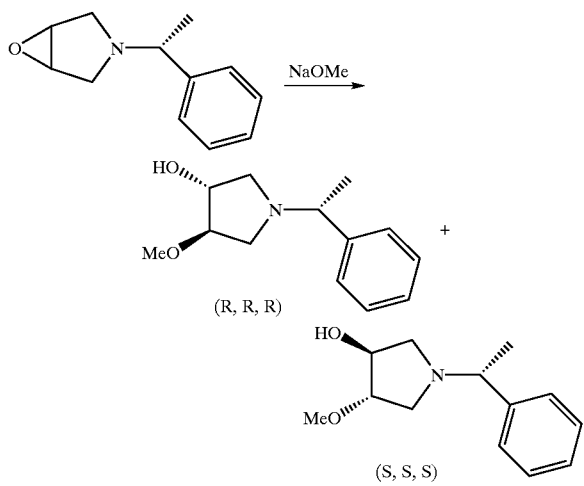

To a solution of (1'R)-1-(1'-phenylethyl)-3,4-epoxypyrrolidine (3.43 kg, 18.1 mol) in methanol (1.72 L) was added a 28% sodium methylate methanol solution (3.84 kg, 19.9 mol), and then 1.72 L of methanol was added thereto. Thereafter, the solution was heated at 70° C. for 3.5 hours under stirring. The reaction was checked by TLC (3% methanol-acetonitrile solution:ammonia water=100:1) and HPLC, and subsequently the reaction mixture was cooled to about room temperature. Thereto were added t-butyl methyl ether (17.2 L) and water (17.2 L), to perform extraction. Thereafter, the aqueous layer was subjected to re-extraction with t-butyl methyl ether (17.2 L). The combined organic layers were washed with 30% salt water, dried over anhydrous magnesium sulfate (1.72 kg), and concentrated under reduced pressure. The solution was subjected to substitution with 1-propanol (7.5 L), and concentrated to give a 1-propanol solution (6.94 kg) containing the captioned compound (3.44 kg) as diastereomer mixtures (yield: 86% on the basis of HPLC quantitative analysis).

$^1$H NMR (400 MHz, CDCl$_3$) (R,R,R)-mer: δ1.36 (3H, d, J=6.8 Hz), 2.32 (1H, broad s,), 2.24 (1H, dd, J=4.4, 10.2 Hz), 2.65 (1H, dd, J=5.4, 9.8 Hz), 2.80 (1H, dd, J=2.9, 10.2 Hz), 2.94 (1H, dd, J=6.8, 10.7 Hz), 3.28 (1H, q, J=6.8 Hz), 3.33 (3H, s), 3.66 (1H, m), 4.19 (1H, broad s), 7.30–1.20 (5H, m) (S,S,R)-mer: δ 1.38 (3H, d, J=6.8 Hz), 2.27 (1H, dd, J=4.4, 9.8 Hz), 2.44 (1H, broad s, 2.45 (1H, dd, J=2.4, 10.2 Hz), 2.64 (1H, dd, J=4.9, 10.3 Hz), 3.23 (1H, dd, J=6.3, 10.3 Hz), 3.28 (1H, q, J=6.8 Hz), 3.35 (3H, s), 3.73 (1H, m), 4.10–4.04 (1H, broad s), 7.30–7.20 (5H, m).

Example 5

(1'S)-1-(1'-phenylethyl)-3-hydroxy-4-methoxy-pyrrolidine

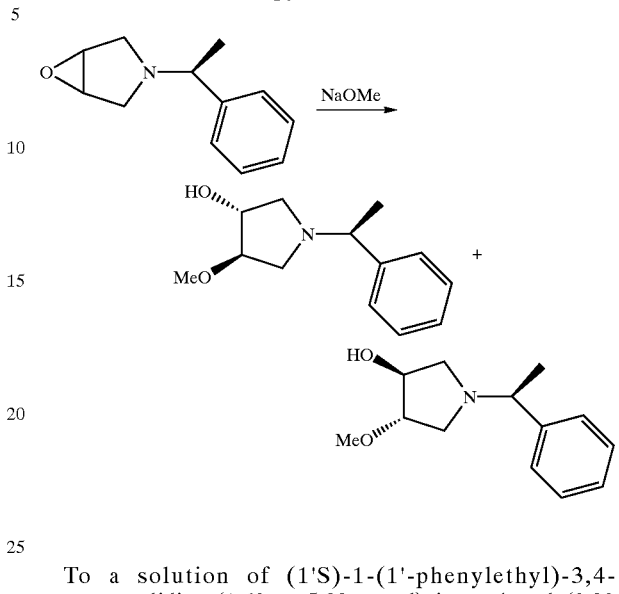

To a solution of (1'S)-1-(1'-phenylethyl)-3,4-epoxypyrrolidine (1.63 g, 5.89 mmol) in methanol (3.20 mL) was added sodium methylate (0.488 g, 8.59 mmol), and then the solution was heated at 70° C. for 6 hours under stirring. The disappearance of the raw materials was determined by TLC (3% methanol-acetonitrile solution:ammonia water=100:1). Thereafter, thereto were added t-butyl methyl ether (8.2 mL) and water (8.2 mL), to perform extraction. Thereafter, the aqueous layer was subjected to extraction with t-butyl methyl ether (8.2 mL) two times. The combined organic layers were washed with saturated salt water (3.26 mL), dried over anhydrous magnesium sulfate, and concentrated under reduced pressure to give 1.92 g of the captioned compound, which consisted of diastereomer mixtures (1:1), as brown oil (yield: 100%).

Example 6

D-dibenzoyltartaric acid salt of (3S,4S)-((1'S)-1-(1'-phenylethyl)-3-hydroxy-4-methoxy-pyrrolidine

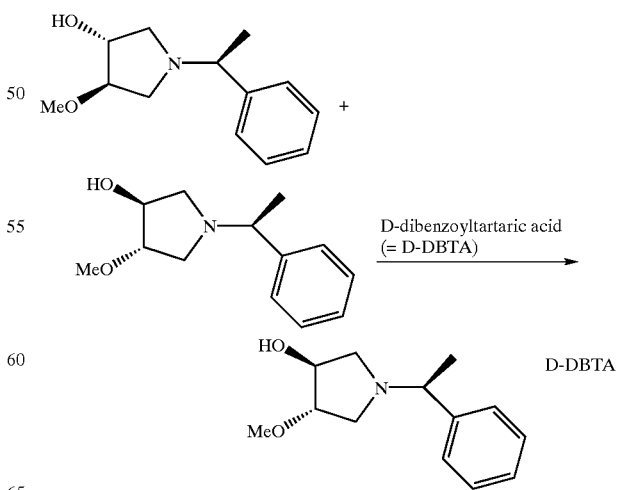

(1'S)-1-(1'-phenylethyl)-3-hydroxy-4-methoxypyrrolidine (1.45 g, 6.54 mmol) was dissolved in ethanol (4.35 ml), and then to this solution was added a solution of D-dibenzoyltartaric acid (monohydrate) (2.85 g, 6.86 mmol) in ethanol (3.0 mL) under stirring. This solution was stirred at 25° C. After 10 minutes, a crystalline salt was precipitated. Thereto was added ethanol (21.7 ml), and further the solution was stirred for 3 hours. The precipitated salt was filtrated under reduced pressure, and washed with ethanol (20 mL) and t-butyl methyl ether (10 mL), each of which was cooled with ice. The salt was dried on the filter under nitrogen stream for 5 minutes, followed by drying under reduced pressure at 35° C. for 1 hour, to give the captioned compound as a white solid (1.29 g, recovery percentage: 34%). The resultant crystal (1.23 g, 2.13 mmol) was dissolved in ethanol (20 mL) at 65° C., and the solution was left at room temperature under stirring. A crystal was precipitated at about 42° C. Ethanol (9.5 mL) was added thereto, and then the solution was cooled to 13° C. The solution was then stirred for 3 hours. The precipitated crystal was collected by filtration. The filtrate was washed with 10 mL of ethanol/t-butyl methyl ether (1:1) and 6 mL of t-butyl methyl ether, and then dried on the filter in flowing air for 30 minutes. The resultant wet body was dried at 40° C. under reduced pressure for 1.5 hour, to give 0.92 g (recovery percentage: 75%) of the captioned compound. By HPLC analysis of free body thereof, the diastereomer excess ratio thereof was 99.9% d.e.

Example 7

(3S,4S)-((1'S)-1-(1'-phenylethyl)-3-hydroxy-4-methoxypyrrolidine

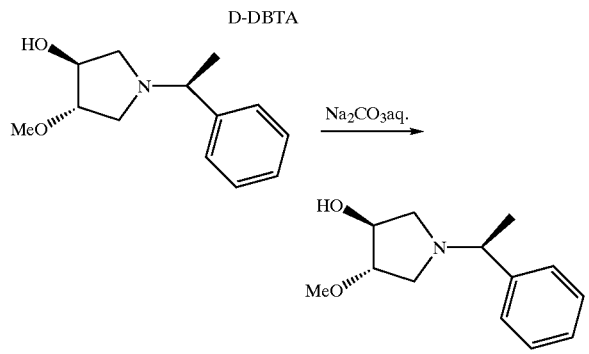

To a suspension of the D-dibenzoyltartaric acid salt (0.82 g, 1.42 mmol) of (3S,4S)-((1'S)-1-(1'-phenylethyl)-3-hydroxy-4-methoxypyrrolidine in t-butyl methyl ether (8 mL) was added a 10% aqueous sodium carbonate solution (6 mL) at 10° C. under stirring, followed by stirring for 20 minutes at 10° C. After separation of the solution into two layers, the aqueous layer was subjected to re-extraction with t-butyl methyl ether (8 mL). The combined organic layers were washed with saturated salt water (3 mL), followed by drying over anhydrous magnesium sulfate, and concentrating under reduced pressure, to give 0.310 g (recovery percentage: 99%) of the captioned compound as a colorless oil material.

Example 8

L-dibenzoyltartaric acid salt of (3R,4R)-((1'R)-1-(1'-phenylethyl)-3-hydroxy-4-methoxy-pyrrolidine

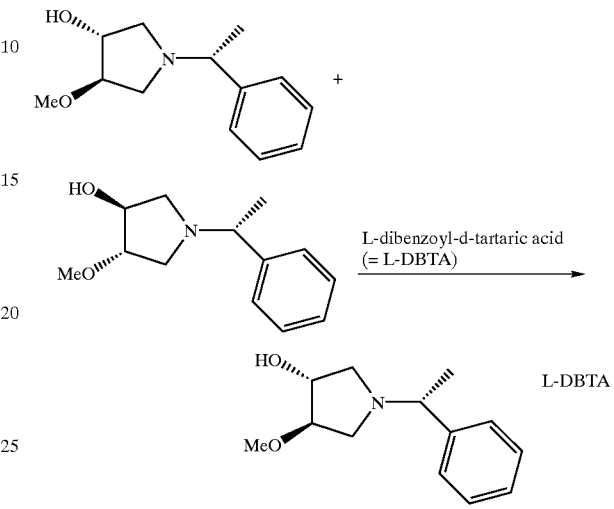

(1'R)-1-(1'-phenylethyl)-3-hydroxy-4-methoxy-pyrrolidine (1.40 g, 6.32 mmol) and L-dibenzoyltartaric acid (monohydrate) (2.50 g, 6.64 mmol) were dissolved in ethanol (23 mL) at 65° C. Under stirring, the solution was cooled in the atmosphere to precipitate a salt at 40° C. Ethanol (5 ml) was added thereto, and the solution was stirred for 12 hours. The solution was stirred in an ice-bath for 5 hours, and then a precipitated salt was collected by filtration. The salt was washed with ethanol/t-butyl methyl ether (2/3, 10 mL), and t-butyl methyl ether (5 mL), each of which was cooled with ice. The salt was dried on the filter under nitrogen stream for 15 minutes, followed by drying under reduced pressure at 40° C. for 2 hours, to give the captioned compound as a white solid (1.46 g, recovery percentage: 40%). The resultant crystal (1.41 g, 2.43 mmol) was dissolved in ethanol (26.5 mL) at 60° C., and then the solution was left at room temperature under stirring. A crystal was precipitated at about 37° C. The solution was cooled to 8° C., and was stirred for 3 hours. Thereafter, the precipitated crystal was collected by filtration, followed by washing with 10 mL of ethanol/t-butyl methyl ether (1:3), and 5 mL of t-butyl methyl ether, and then drying on the filter under air stream for 30 minutes. The resultant wet body was dried at 40° C. under reduced pressure for 1 hour, to give 1.11 g (recovery percentage: 78.6%) of the captioned compound.

$^1$H NMR (400 MHz, DMSO-$d_6$) δ 1.36 (3H, d, J=6.8 Hz), 3.10–2.50 (4H, m), 3.23 (3H, s), 3.70–3.58 (1H, m), 4.10–4.00 (1H, m), 5.75 (2H, s), 7.40–7.30 (5H, m), 7.53 (4H, dd, J=7.8, 7.8 Hz), 7.66 (2H, dd, J=7.8, 7.8 Hz), 8.29 (4H, dd, J=7.8, 7.8 Hz).

Example 9

L-dibenzoyltartaric acid salt of (3R,4R)-((1'R)-1-(1'-phenylethyl)-3-hydroxy-4-methoxy-pyrrolidine

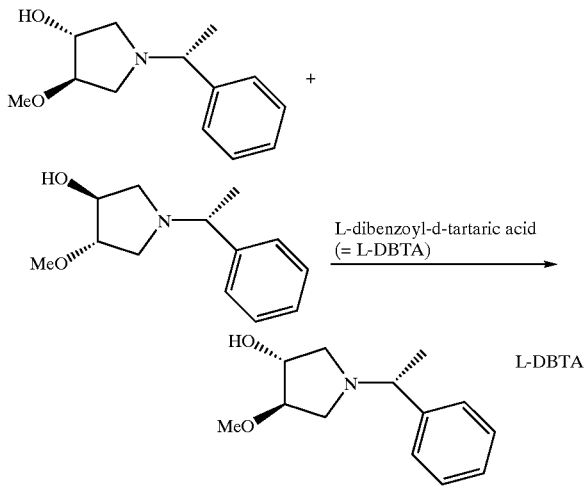

(1'R)-1-(1'-phenylethyl)-3-hydroxy-4-methoxy-pyrrolidine (20 g, 0.904 mol) and L-dibenzoyltartaric acid (monohydrate) (34.0 g, 0.904 mol) were dissolved in propanol (300 mL) at 40° C. Under stirring, the solution was left at room temperature, to precipitate a salt at 25° C. The precipitated crystal was collected by filtration, and washed with propanol. The crystal was dried on the filter under air stream for 15 minutes (20.9 g, recovery percentage: 40%). The resultant crystal (20.0 g) was dissolved in propanol (300 mL) at 60° C. The solution was cooled under stirring in the atmosphere. The solution was cooled to 25° C., and then stirred for 3 hours. The precipitated crystal was collected by filtration, washed with propanol, and dried on the filter in flowing air for 30 minutes. The resultant wet body was dried at 40° C. under reduced pressure for 1 hour, to give 15.7 g (recovery percentage: 78.5%) of the captioned compound.

Example 10

((3R,4R)-((1'R)-1-(1'-phenylethyl)-3-hydroxy-4-methoxypyrrolidine

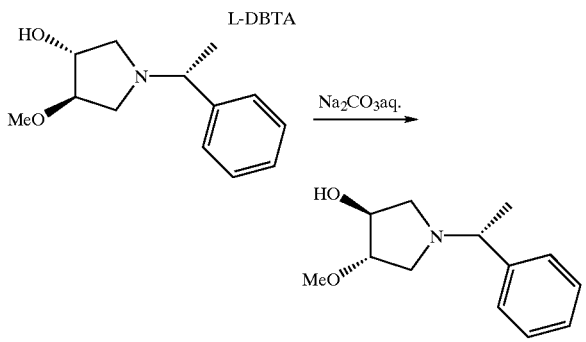

A mixed solution of a 10% aqueous sodium carbonate solution (7.3 mL) and t-butyl methyl ether (10 mL) was stirred at 10° C., and to this solution was added an L-dibenzoyltartaric acid salt (1.0 g, 1.72 mmol) of (3R,4R)-((1'R)-1-(1'-phenylethyl)-3-hydroxy-4-methoxypyrrolidine. The solution was stirred at 10° C. for 50 minutes. After separation of the solution into two layers, the aqueous layer was subjected to re-extraction with t-butyl methyl ether (10 mL). The combined organic layers were washed with saturated salt water (3 mL), followed by drying over anhydrous magnesium sulfate, and concentrating under reduced pressure, to give 0.379 g recovery percentage: 99.5%) of the captioned compound as a colorless oily material. By HPLC analysis, the diastereomer excess ratio thereof was 100% d.e.

$^1$H NMR (400 MHz, CDCl$_3$) δ 1.36 (3H, d, J=6.8 Hz), 2.32 (1H, br-s), 2.24 (1H, dd, J=4.4, 10.2 Hz), 2.65 (1H, dd, J=5.4, 9.8 Hz), 2.80 (1H, dd, J=2.9, 10.2 Hz), 2.94 (1H, dd, J=6.8, 10.7 Hz), 3.28 (1H, q, J=6.8 Hz), 3.33 (3H, s), 3.66 (1H, m), 4.19 (1H, broad s), 7.30–7.20 (5H, m).

Example 11

(3S,4S)-3-hydroxy-4-methoxypyrrolidine hydrochloride

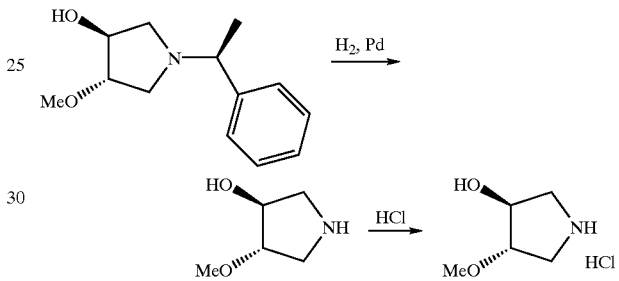

((3S,4S)-((1'S)-1-(1'-phenylethyl)-3-hydroxy-4-methoxypyrrolidine (0.310 g, 1.40 mmol) was dissolved in methanol (1.5 mL), and then thereto was added 93 mg (weight corresponding to dry material: 46.5 mg) of 20% palladium hydroxide-carbon (containing 50% of water). Thereafter, the solution was stirred at 20° C. for 5 hours and at 35° C. for 3 hours in the atmosphere of hydrogen. The catalyst was filtered off, and the filtrate was concentrated under reduced pressure to yield a deprotected body (0.164 g, yield: 100%) as a colorless crystal.

The resultant oily material (0.164 g) was dissolved in methanol (1 mL). Thereto was dropwise added a 4 mol/L hydrochloric acid-ethyl acetate solution (0.54 mL) under cooling with ice, and then the solution was stirred at the same temperature for 5 minutes. The solution was concentrated at 40° C. under reduced pressure. Thereafter, 2-propanol (1 mL) was added to the solidified residue, and the residue was dissolved at 65° C. The solution was cooled under stirring in the atmosphere and then was cooled with ice. The solution was then stirred for 1.5 hours. The precipitated crystal was collected by filtration, and dried to yield 0.129 g of the captioned compound as a colorless crystal (yield: 60%).

$[α]^{20}_{405\ nm}$ −12.0 (c 2.52, MeOH)

$^1$H NMR (400 MHz, DMSO-d$_6$) δ: 3.05 (1H, d, J=12.7 Hz), 3.14 (1H, d, J=3.9 Hz), 3.18 (1H, d, J=12.4 Hz), 3.24 (1H, d, J=3.9 Hz), 3.28 (3H, s), 3.80 (1H, d, J=3.4 Hz), 4.25 (1H, d, J=3.4 Hz), 5.70 (1H, broad s), 9.41 (1H, broad s), 9.46 (1H, broad s).

Example 12

(3R,4R)-3-hydroxy-4-methoxypyrrolidine hydrochloride

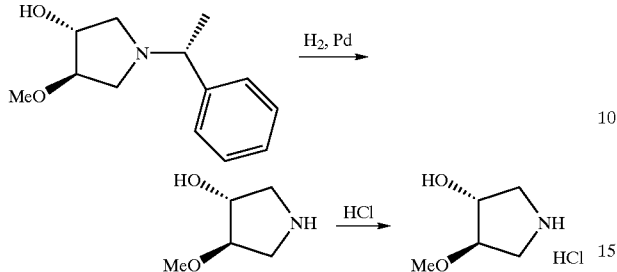

((3R,4R)-((1'R)-1-(1'-phenylethyl)-3-hydroxy-4-methoxypyrrolidine (0.300 g, 1.36 mmol) was dissolved in methanol (1.5 mL), and then thereto was added 90 mg (weight corresponding to dry material: 45 mg) of 20% palladium hydroxide-carbon (containing 50% of water). Thereafter, the solution was stirred at 40°0 C. in the atmosphere of hydrogen for 6 hours. The catalyst was filtered off, and the filtrate was concentrated under reduced pressure to yield a deprotected body (0.146 g, yield: 92%) as a colorless crystal. The resultant deprotected body (0.146 g) was dissolved in methanol (1 mL). Thereto was dropwise added a 10% hydrochloric acid-methanol solution (1 mL) under cooling with ice, and then the solution was stirred at the same temperature for 5 minutes. The solution was concentrated at 40° C. under reduced pressure. Thereafter, 2-propanol (1 mL) was added to the residue, and then solution was again concentrated. Thereto was added 2-propanol (1 mL), and the residue was dissolved at 70° C. The solution was cooled under stirring in the atmosphere and then was cooled with ice. The solution was then stirred for 1 hour. The precipitated crystal was collected by filtration, and dried to yield 0.084 g (yield: 44%) of the captioned compound as a colorless crystal.

$[\alpha]^{20}_{405\ nm}$+11.0 (c 2.52, MeOH)

Example 13

(3R,4R)-3-hydroxy-4-methoxypyrrolidine oxalate

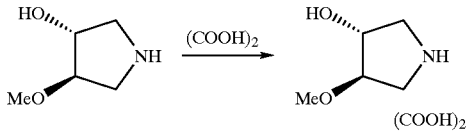

To 8.8 mL of ethanol was added 583 mg (5 mmol) of (3R,4R)-3-hydroxy-4-methoxypyrrolidine obtained by the above-mentioned procedure, and then thereto was added a solution of oxalic acid dihydrate (627 mg, 5 mmol) in ethanol (3 mL) at room temperature. After 1 hour, the precipitated crystal was collected by filtration, washed with 2 mL of ethanol, and dried under reduced pressure at 40° C., to give 732 mg (yield: 78%) of the target oxalic acid salt.

$^1$H NMR (400 MHz, DMSO-d$_6$) δ: 3.05 (1H, d, J=12.4 Hz), 3,17 (1H, dd, J=4.0, 12.4 Hz), 3.24 (1H, d, J=12.4 Hz), 2.27 (3H, s), 3,27 (1H, dd, J=4.0, 12.4 Hz), 3.78 (1H, d, J=3.6 Hz), 4.24 (1H, d, J=3.6 Hz).

Example 2-1

(6-(3R,4R)-3-hydroxy-4-methoxypyrrolidine)-2-benzylpyridine

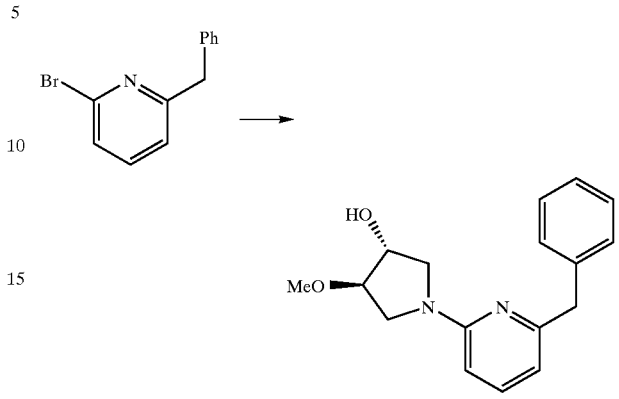

In the atmosphere of nitrogen, to a 2L four necked flask were added (3R,4R)-3-hydroxy-4-methoxypyridine (106 g, 0.91 mol), 6-bromo-2-benzylpyridine (150 g, 0.605 mol) [see Tetrahedron Letters, 21, pp. 845–848 (1980)], 1,8-diazabicyclo[5.4.0]-undeca-5-ene (92 g, 0.605 mol) and N-methylpyrrolidone (150 mL). Then, under stirring, the solution was heated in an oil bath at 110° C. for 11 hours. (3R,4R)-3-hydroxy-4-methoxypyridine (10.6 g, 0.09 mol) was added thereto. Under stirring, the solution was heated in an oil bath of 110° C. for 1 hour. The solution was left at room temperature, and then thereto were added 450 mL of t-butyl methyl ether and 450 mL of water. While the temperature of the inside was kept at 20° C. or less by an ice bath, 2 N hydrochloric acid was dropwise added to the solution until the pH of the solution was 6. The solution was transferred to a 2 L separatory funnel. The upper layer was separated, and the remaining aqueous layer was again subjected to extraction with 300 mL of t-butyl methyl ether. The t-butyl methyl ether layers were combined, followed by washing with 300 mL of water and 300 mL of saturated salt water. The upper layer was dried over anhydrous magnesium sulfate, and washed with 100 mL of t-butyl methyl ether. The filtrate was concentrated under reduced pressure at 40° C. to give 171 g (crude yield: 99.6%) of the captioned compound as a black brown oily material.

$^1$H-NMR (400 MHz, CDCl$_3$) δ: 3.42 (3H, s), 3.49 (1H, dd, J=3, 12 Hz), 3.52 (1H, dd, J=3, 12 Hz), 3.71 (1H, dd, J=5, 12 Hz), 3.75 (1H, dd, J=5, 12 Hz), 3.85–3.88 (1H, m), 3.97 (2H, s), 4.38–4.40 (1H, m), 6.16(1H, d, J=8 Hz), 6.35(1H, d, J=8 Hz), 7.17–7.34 (6H, m)

Example 2-2

(6-(3R,4R)-3-hydroxy-4-methoxypyrrolidine-1-yl)-3-bromo-2-benzylpyridine

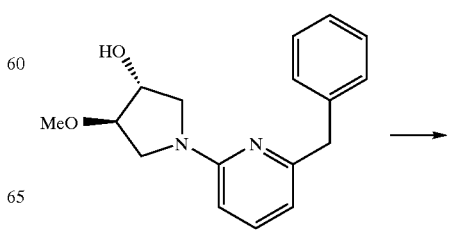

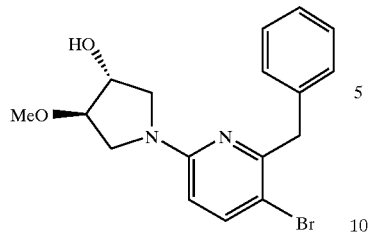

A solution of (6-(3R,4R)-3-hydroxy-4-methoxypyrrolidine)-2-benzylpyridine (2 g, 7 mmol) in N,N-dimethylformamide (8 mL) was stirred in an ice bath. N-bromosuccinimide (1.3 g, 7.4 mol) was added little by little to the solution. Thereto was added t-butyl methyl ether (100 mL) to separate the solution into two layers. The upper layer was washed with 100 mL of an aqueous 5% sodium thiosulfate solution, and saturated salt water. The layer was dried over anhydrous magnesium sulfate, concentrated under reduced pressure, and purified by silica gel chromatography (developing solution: hexane: ethyl acetate=3:1) to yield 2.1 g (yield: 83%) of the captioned compound as an oily material.

$^1$H-NMR (400 MHz, CDCl$_3$) δ: 3.41 (3H, s), 3.42–3.50 (2H, m), 3.64–3.71 (2H, m), 3.84–3.86 (1H, m), 4.15 (2H, s), 4.39–4.41 (1H, m), 6.09 (1H, d, J=9 Hz), 7.18 (1H, dd, J=8, 8 Hz), 7.26 (2H, dd, J=8, 8 Hz), 7.36 (2H, d, J=8 Hz), 7.48 (1H, d, J=8 Hz).

Example 2-3

(3R)-3-[2-benzyl-6-[(3R,4R)-3-hydroxy-4-methoxypyrrolidine-1-yl]pyridine-3-yl]ethynyl]quinuclidine-3-ol

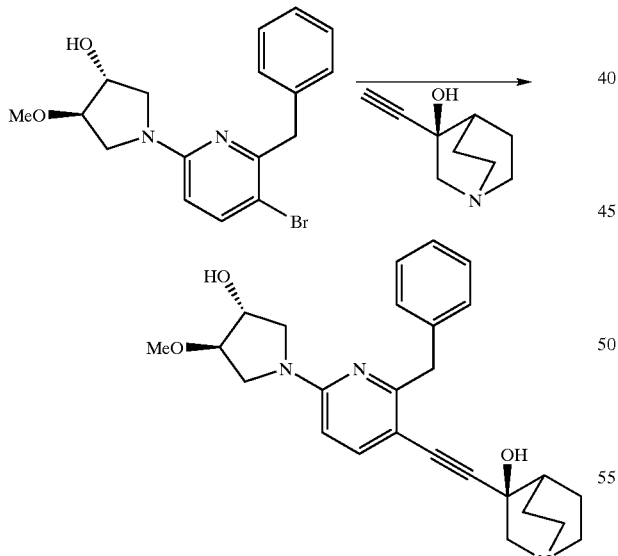

(6-(3R,4R)-3-hydroxy-4-methoxypyrrolidine-1-yl)-3-bromo-2-benzylpyridine (1.14 g, 3 mmol), (3R)-quinuclidine-3-ol (680 mg, 4.5 mmol), and triphenylphosphine (79 mg, 0.3 mmol) were dissolved in 10 mL of piperidine. Thereto were added palladium tetrakis(triphenylphosphine) (173 mg, 0.15 mmol) and copper iodide (57 mg, 0.3 mmol), and then the solution was heated at 100° C. for 5 hours. To the reaction solution were added tetrahydrofuran and ethyl acetate, and the resultant solution was washed with water. Thereafter, anhydrous magnesium sulfate was added to the solution so as to dry the solution. The filtrate was concentrated under reduced pressure to yield an oily material containing the captioned compound.

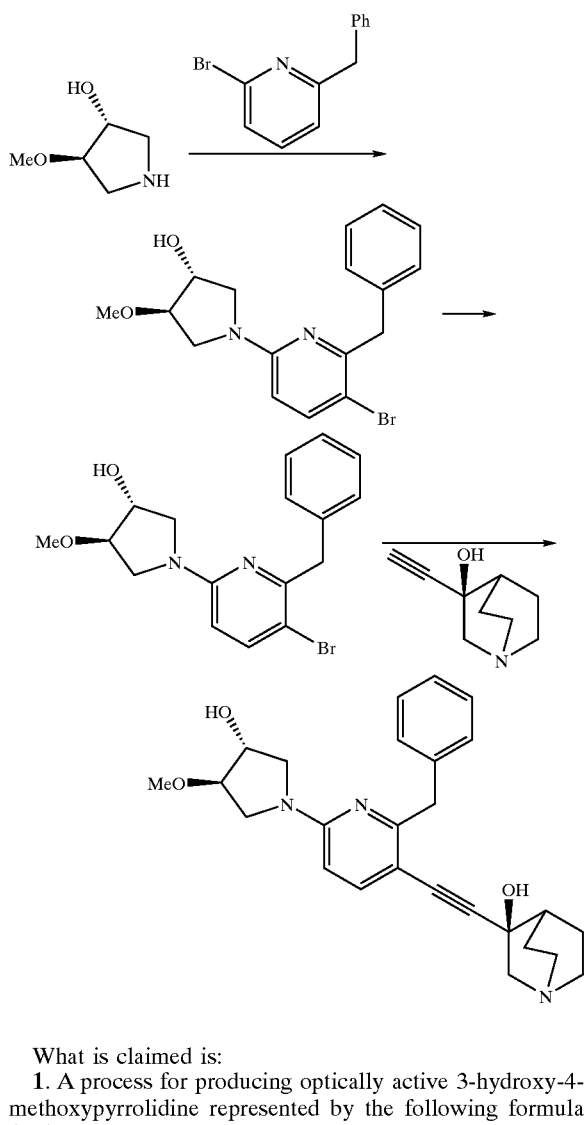

What is claimed is:

1. A process for producing optically active 3-hydroxy-4-methoxypyrrolidine represented by the following formula (1-7):

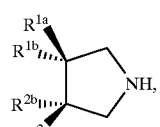

wherein $R^{1a}$ and $R^{1b}$ are different from each other, and each of $R^{1a}$ and $R^{1b}$ represents a hydrogen atom or a hydroxyl group, and $R^{2a}$ and $R^{2b}$ are different from each other, and each of $R^{2a}$ and $R^{2b}$ represents a hydrogen atom or a methoxy group, a salt thereof or a hydrate thereof, comprising the steps of:

mixing a pyrrolidine derivative selected from the group consisting of a mixture of pyrrolidine derivatives represented by the following formula (1-4):

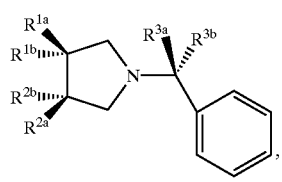
(1-4)

wherein $R^{1a}$, $R^{1b}$, $R^{2B}$ and $R^{2b}$ have the same definition as mentioned above, and each of $R^{3a}$ and $R^{3b}$ represents a hydrogen atom or a methyl group, with an optically active dibenzoyltartaric acid derivative represented by the following formula (1-5):

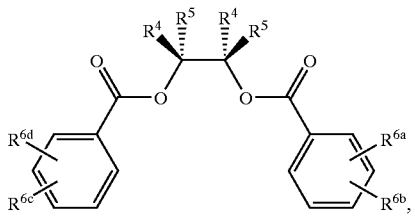
(1-5)

wherein $R^{6a}$, $R^{6b}$, $R^{6c}$ and $R^{6d}$ each independently represents a hydrogen atom, a halogen atom, a C1–6 alkoxy group or a C1–6 alkyl group, and $R^4$ and $R^5$ are different from each other, and each of $R^4$ and $R^5$ represents a hydrogen atom or a carboxyl group, to obtain a mixture of salts of the pyrrolidine derivative and the optically active dibenzoyltartaric acid derivative, followed by crystallization to obtain a salt from the mixture of salts, removal of the optically active dibenzoyltartaric acid derivative from the salt, and extraction with an organic solvent, to yield a compound (1-6) represented by the following formula (1-6):

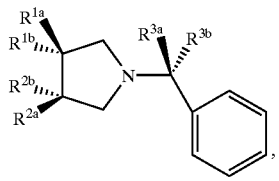
(1-6)

wherein $R^{1a}$, $R^{1b}$, $R^{2a}$, $R^{2b}$, $R^{3a}$ and $R^{3b}$ have the same definition as mentioned above; and
removing the 1-phenylethyl group of the compound (1-6), to yield the optically active 3-hydroxy-4-methoxypyrrolidine.

2. The method according to claim 1, wherein each of $R^{1a}$ and $R^{2b}$ represents a hydrogen atom.

3. The method according to claim 1, wherein each of $R^{1b}$ and $R^{2a}$ represents a hydrogen atom.

4. The method according to claim 1, wherein $R^{3a}$ represents a methyl group.

5. The method according to claim 1, wherein $R^{3b}$ represents a methyl group.

6. The method according to claim 1, wherein said pyrrolidine derivative is a mixture of compounds represented by the following formulae (1-4a) and (1-4b) (wherein $R^{3a}$ and $R^{3b}$ are different from each other, and each of $R^{3a}$ and $R^{3b}$ represents a hydrogen atom or a methyl group):

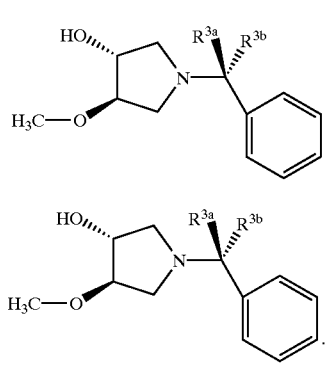
(1-4a)

(1-4b)

7. The method according to claim 6, wherein said mixture of said compounds (1-4a) and (1-4b) is in a ratio of 1:1 of (1-4a) to (1-4b).

8. The method according to claim 1, wherein $R^4$ represents a hydrogen atom.

9. The method according to claim 1, wherein $R^5$ represents a hydrogen atom.

10. The method according to claim 1, wherein each of $R^{6a}$, $R^{6b}$, $R^{6c}$ and $R^{6d}$ represents a hydrogen atom.

11. A process for producing optically active 3-hydroxy-4-methoxypyrrolidine represented by the following formula (1-7):

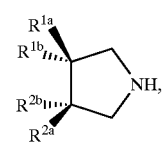
(1-7)

wherein $R^{1a}$ and $R^{1b}$ are different from each other, and each of $R^{1a}$ and $R^{1b}$ represents a hydrogen atom or a hydroxyl group, and $R^{2a}$ and $R^{2b}$ are different from each other, and each of $R^{2a}$ and $R^{2b}$ represents a hydrogen atom or a methoxy group, a salt thereof or a hydrate thereof, comprising the steps of:
reacting an oxysilane derivative represented by the following formula (1-1):

(1-1)

wherein $L^1$ represents a halogen atom, a methanesulfonyloxy group, or a p-toluenesulfonyloxy group, with an amine derivative represented by the following formula (1-2)

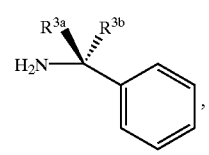
(1-2)

wherein $R^{3a}$ and $R^{3b}$ are different from each other, and each of $R^{3a}$ and $R^{3b}$ represents a hydrogen atom or a methyl group, to yield a pyrrolidine derivative (1-3) represented by the following formula (1-3):

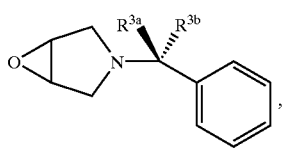

(1-3)

wherein $R^{3a}$ and $R^{3b}$ have the same definition as mentioned above;

reacting the derivative (1-3) with a methoxylating agent, to yield a mixture of pyrrolidine derivatives represented by the following formula (1-4):

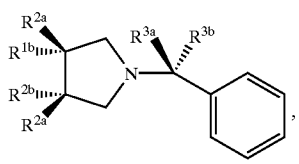

(1-4)

wherein $R^{1a}$, $R^{1b}$, $R^{2a}$, $R^{2b}$, $R^{3a}$ and $R^{3b}$ have the same definition as mentioned above;

mixing the mixture with an optically active dibenzoyltartaric acid derivative represented by the following formula (1-5):

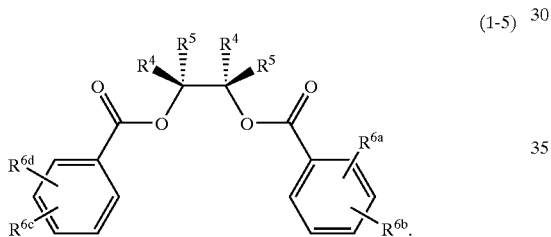

(1-5)

wherein $R^{6a}$, $R^{6b}$, $R^{6c}$ and $R^{6d}$ each independently represents a hydrogen atom, a halogen atom, a C1–6 alkoxy group or a C1–6 alkyl group, and $R^4$ and $R^5$ are different from each other, and each of $R^4$ and $R^5$ represents a hydrogen atom or a carboxyl group, to obtain a mixture of salts of the pyrrolidine derivative and the optically active dibenzoyltartaric acid derivative, followed by crystallization to obtain a salt from the mixture of salts, removal of the optically active dibenzoyltartaric acid derivative from the salt, and extraction with an organic solvent, to yield a compound (1-6) represented by the following formula (1-6):

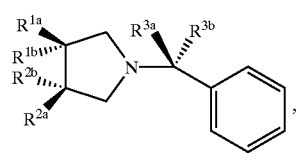

(1-6)

wherein $R^{1a}$, $R^{1b}$, $R^{2a}$, $R^{2b}$, $R^{3a}$ and $R^{3b}$ have the same definition as mentioned above; and removing the 1-phenylethyl group of the compound (1-6), to yield optically active the 3-hydroxy-4-methoxypyrrolidine.

12. The method according to claim 11, wherein each of $R^{1a}$ and $R^{2b}$ represents a hydrogen atom.

13. The method according to claim 11, wherein each of $R^{1b}$ and $R^{2a}$ represents a hydrogen atom.

14. The method according to claim 11, wherein $R^{3a}$ represents a methyl group.

15. The method according to claim 11, wherein $R^{3b}$ represents a methyl group.

16. The method according to claim 11, wherein said mixture of pyrrolidine derivatives is a mixture of compounds represented by the following formulae (1-4a) and (1-4b) (wherein $R^{3a}$ and $R^{3b}$ are different from each other; and each of $R^{3a}$ and $R^{3b}$ represents hydrogen atom or a methyl group):

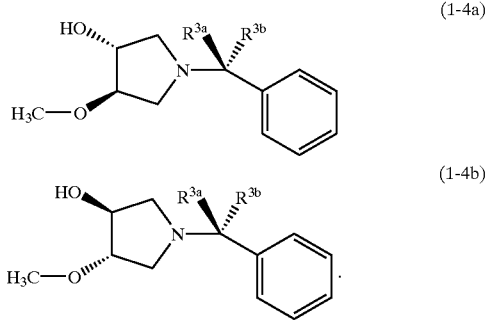

(1-4a)

(1-4b)

17. The method according to claim 16, wherein said mixture of said compounds (1-4a) and (1-4b) is in a ratio of 1:1 of (1-4a) to (1-4b).

18. The method according to claim 11, wherein $R^4$ represents a hydrogen atom.

19. The method according to claim 11, wherein $R^5$ represents a hydrogen atom.

20. The method according to claim 11, wherein each of $R^{6a}$, $R^{6b}$, $R^{6c}$ and $R^{6d}$ represents a hydrogen atom.

* * * * *